United States Patent [19]

Morscher et al.

[11] Patent Number: 5,108,439

[45] Date of Patent: Apr. 28, 1992

[54] CENTERING ELEMENT FOR A SHANK OF A JOINT ENDOPROSTHESIS

[75] Inventors: Erwin W. Morscher, Basel; Roland Willi, Stadel; Rudolf Koch, Berlingen, all of Switzerland

[73] Assignees: Sulzer Brothers Limited, Winterthur; Protek AG, Berne, both of Switzerland; a part interest

[21] Appl. No.: 757,892

[22] Filed: Sep. 11, 1991

[30] Foreign Application Priority Data

Oct. 25, 1990 [CH] Switzerland .................. 03398/90

[51] Int. Cl.⁵ .......................... A61F 2/30; A61F 2/36
[52] U.S. Cl. ......................... 623/18; 623/16; 623/23
[58] Field of Search ............. 623/16, 18, 20, 22, 623/23, 16 A

[56] References Cited

U.S. PATENT DOCUMENTS 3,793,650  2/1974  Ling et al. ........................... 623/18
4,268,920  5/1981  Engelbrecht et al. ............. 623/18 X
4,888,023  12/1989  Averill et al. ......................... 623/22
4,936,859  6/1990  Morscher et al. .................... 623/18

FOREIGN PATENT DOCUMENTS 0290735  11/1988  European Pat. Off. .
0315286   5/1989  European Pat. Off. ............. 623/22
0427444   5/1991  European Pat. Off. .
3314210   1/1984  Fed. Rep. of Germany .
2632182  12/1989  France ................................. 623/18
2104391   3/1983  United Kingdom .

*Primary Examiner*—Ronald Frinks
*Attorney, Agent, or Firm*—Kenyon & Kenyon

[57] ABSTRACT

A centering element for a shank of a femur bone prosthesis is of three-sided pyramidal shape with an equilateral triangular-shaped base. The apex of the centering element is also rounded while a stud is provided at the base for interfitting in a recess in the prosthesis shank. The shape of the centering element enables insertion of the element together with a shank in a cavity in a bone already filled with bone cement.

18 Claims, 1 Drawing Sheet

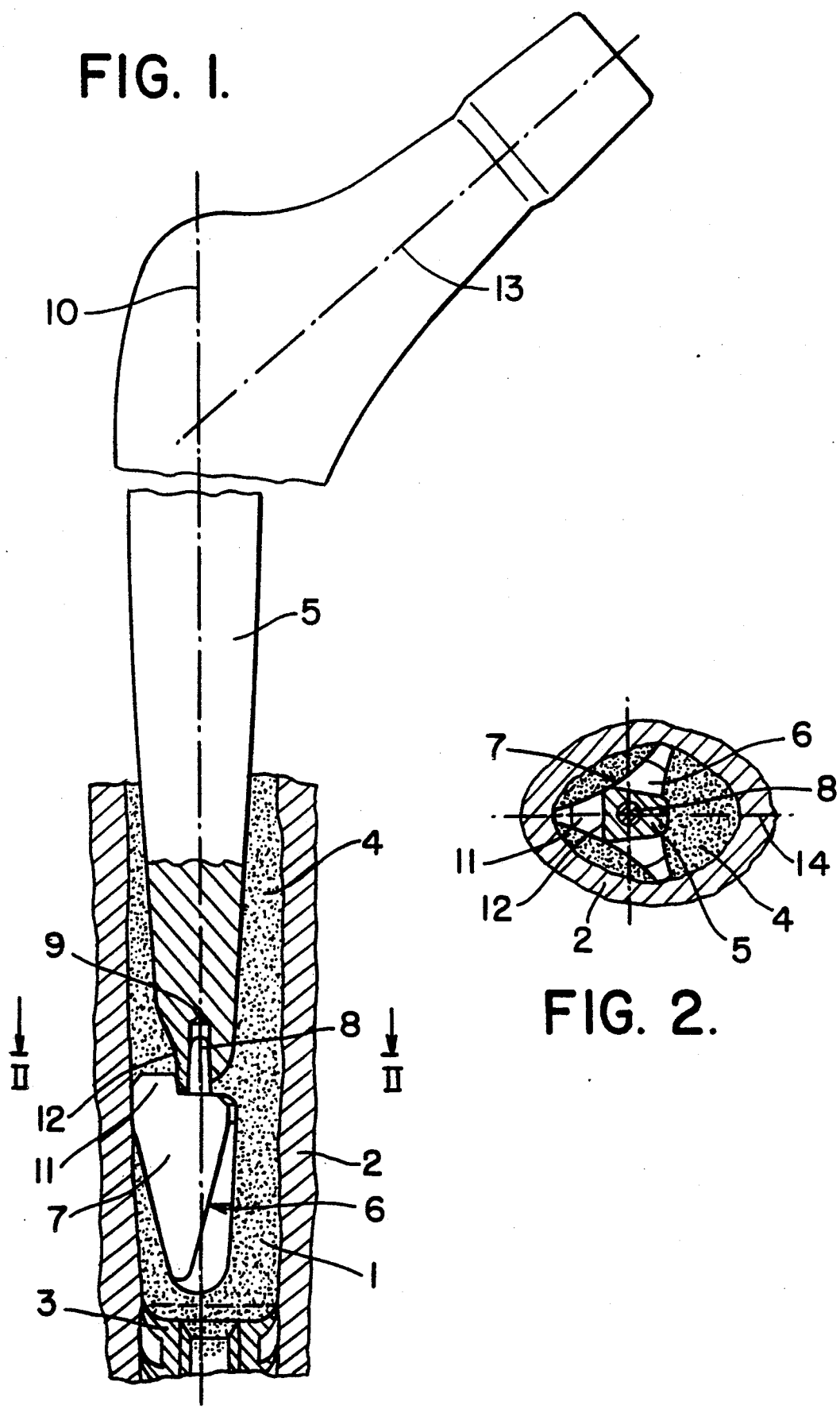

CENTERING ELEMENT FOR A SHANK OF A JOINT ENDOPROSTHESIS

This invention relates to a centering element for a shank of a joint endoprosthesis.

Heretofore, various types of centering elements have been known for centering the shank of a joint endoprosthesis in an operatively created cavity in a bone. Generally, the centering elements have been employed about the free end of the shank so that the shank may be implanted in a bed of bone cement with the most uniform thickness of bone cement about the circumference of the shank.

For example, European Patent Application 0 315 283 describes a centering element which can be disposed about a distal end of a shank of a femur head prosthesis together with a similar centering element on a proximal region of the prosthesis. As with other known centering elements, in order to also serve as a closure for the bone cement, the centering elements fill out the whole cross-section of the operational bone cavity. Accordingly, such centering elements must be inserted before the bone cement is introduced into the bone. Generally, such centering elements are not suitable for implantation techniques wherein, as is usual in most cases, the prosthesis and the element for distal centering of the prosthesis are inserted into a bone cavity after the cavity has been filled with bone cement.

Other types of centering elements have also been known, for example, from published U.K. Patent Application 2 104 391 wherein a body is provided with a plurality of radially extending resilient members for engaging the sides of a medullary canal to hold a shank away from the sides of a medullary canal. A similar structure is also described in French Patent 2 632 182. However, in either case, if the centering element were to be pushed into a bone cement bed, the resistance of the bone cement can distort the resilient elements in a differential manner relative to each other so that an accurate centering of the prosthesis shank is impaired.

Still other types of centering elements have been known such as described in German OS 33 14 210 wherein a centering element is formed on a closure element so as to be positioned prior to formation of a bone cement bed and implanting of a shank.

Accordingly, it is an object of the invention to provide a centering element for a shank of a joint endoprosthesis which can be readily implanted into a bone cement bed along With the endoprosthesis.

It is another object of the invention to provide a centering element of relatively simple construction.

It is another object of the invention to obtain a simplified technique for centering a shank of a joint endoprosthesis in a surgically prepared bone cavity having a bone cement bed therein.

Briefly, the invention provides a centering element for a shank of a joint endoprosthesis which is of three-sided pyramid shape with an equilateral triangular shaped base for connecting the element to a shank of the joint endoprosthesis.

With the centering element connected to a shank of a joint endoprosthesis, both the shank and centering element can be inserted into a bone cement bed within a prepared cavity of a bone. Upon insertion, the bone cement which is usually prevented from further penetration into the bone at the end of the operationally created cavity by a known closure for the cement or the medullary canal, is displaced along the sides of the three-sided pyramidal centering element into the space between the shank and the bone. Thus, the shank and centering element may be inserted without difficulties into the cement-filled cavity.

The flow of the bone cement and the insertion of the centering element are facilitated if the sides of the centering element have a concave curvature and/or the apex of the element is rounded.

The means for connecting the centering element to the shank may include a stud on one of the element and shank and a recess in the other of the element and shank for receiving the stud. For example, the stud may project from the centering element while being plugged into the corresponding recess in a distal end of the shank. Further, the stud and recess may be arranged to be concentric, i.e., coaxial with the axis of the centering element as well as with the longitudinal axis of the shank of the prosthesis.

In the case of a femur head prosthesis, it is important that one corner of the centering element point in the lateral direction in order to be able to keep the proportion of cement there up to the most definite thickness possible. This may be achieved, for example, if one corner of the centering element is provided with a nose-like extension which projects from the base and rests against a laterally-directed contact area on the distal end of the shank. The extension and the contact area may, in that case, serve additionally as an interfitting means to prevent relative rotation between the centering element and shank, i.e., twisting of the centering element on the shank.

These and other objects and advantages of the invention will become more apparent from the following detailed description taken in conjunction with the accompanying drawings wherein:

FIG. 1 illustrates a view of a centering element according to the invention mounted on a shank of a femur head prosthesis within a bone cavity; and FIG. 2 illustrates a view taken on line II—II of FIG. 1.

Referring to FIG. 1, a centering element 6 is constructed as a solid body with a three-sided pyramid shape with an equilateral triangular-shaped base (see FIG. 2). As indicated, each side 7 of the element 6 is of concave curvature. In addition, each corner formed by two sides of the element 6 is of generally flat or rounded shape leading to a rounded apex (see FIG. 1). Also, a flat, shown vertical in FIG. 1, is provided at the upper end, as viewed, of each corner for engaging against the inside wall of a bone 2.

As indicated in FIG. 1, the centering element 6 is constructed to be used in combination with a shank 5 of a joint endoprosthesis, such as a femur head prosthesis. The shank 5 is disposed along a longitudinal axis 10 and is joined with a neck which extends from the shank 5 along a second axis 13 disposed in a common plane 14 (see FIG. 2) with the axis 10 of the shank.

The unit composed of the centering element 6 and the shank 5 is sized so as to be inserted into an operatively created cavity 1 in a long bone 2 such as a femur. As indicated, a closure 3 to the medullary canal or for a bone cement 4 is inserted at the end of the cavity 1 furthest from the prosthesis. This closure 3 serves to prevent movement of the bone cement 4 into the bone 2 when the shank 5 and centering element 6 are inserted into the cement-filled cavity 1.

As shown, a means is provided on the centering element 6 for connecting the element 6 to the shank 5. For example, the means includes a stud 8 which projects from the base of the centering element 6 and a recess 9 in the distal end of the shank 5 for receiving the stud 8, for example, in a friction fit manner. The stud 8 and the recess 9 may be slightly tapered in order to improve the "adhesion" of the "connection." As indicated, the stud 8 and recess 9 are arranged to be coaxial with the longitudinal axis 10 of the shank. This facilitates centering of the shank. Obviously, a reversal of the arrangement of the stud 8 and recess 9 or other constructions for the connecting means are possible.

During use, after the bone cement 4 has been placed in the cavity 1, the centering element 6 and interconnected shank 5 are inserted. At this time, the centering element penetrates into the bone cement 4 with the rounded apex and curved sides 7 facilitating insertion. Due to the concave curvature of the sides 7, the "free cross-section" for the "flow" of the bone cement 4 is increased. Further, as illustrated in FIG. 2, the three corners of the centering element engage against the inside wall of the bone so as to firmly center the element 6 and, thus, the shank 5 within the bone 2.

In the case of the femur head prosthesis, it is important that one corner of the centering element 6 point in the lateral direction. In order to insure this, the shank 5 is provided with a contact area 12 at the distal end which is perpendicular to the common plane 14 defined by the longitudinal axis 10 and neck axis 13. In addition, the centering element 6 is provided with a noselike extension 11 which projects upwardly, as viewed in FIG. 1, from the base and which abuts the contact area 12 in order to align one corner of the element 6 in the common plane 14 and laterally of the neck. As indicated in FIG. 2, a normal to the contact area 12 is directed laterally within the common central plane 14 defined by the longitudinal axis 10 and the axis 13 of the neck. Alternatively, other structural means may be used for aligning one corner of the centering element 6 laterally of the shank 5. The noselike extension 11 and the contact area 12 also serve as a means for interfitting the centering element 6 with the shank 5 in order to prevent relative rotation therebetween.

The invention thus provides a centering element of relatively simple construction which is able to not only center a shank within a bone cavity but also facilitates insertion of the centering element and shank into a bone cement in the cavity.

What is claimed is:

1. A centering element for a shank of a joint endoprosthesis, said element having a three-sided pyramidal shape with an equilateral triangular shaped base and means on said base for connecting said element to a shank of a joint endoprosthesis.

2. A centering element as set forth in claim 1 wherein each side is of concave curvature.

3. A centering element as set forth in claim 1 having a rounded apex.

4. A centering element as set forth in claim 1 wherein said means includes a stud projecting from said base.

5. A centering element as set forth in claim 4 wherein said stud is disposed on a central longitudinal axis of said element.

6. A centering element for a shank of a joint endoprosthesis, said element being a solid body having a three-sided pyramidal shape with an equilateral triangular shaped base, each said side of said body being of concave curvature and each pair of adjacent sides forming a flat for engaging against an inside wall of a bone.

7. A centering element as set forth in claim 6 having a rounded apex.

8. A centering element as set forth in claim 6 having a nose like extension on said base for interfitting with a shank of a joint endoprosthesis to prevent rotation therebetween.

9. A centering element as set forth in claim 6 having a stud on a central longitudinal axis of said element for connection to a shank of an endoprosthesis.

10. In combination,
a shank of a joint endoprosthesis;
a centering element for centering said shank in a bone cavity, said centering element having a three-sided pyramidal shape with an equilateral triangular shaped base; and
means for connecting said element to a distal end of said shank.

11. The combination as set forth in claim 10 wherein said means includes a stud on one of said element and said shank and a recess in the other of said element and said shank receiving said stud.

12. The combination as set forth in claim 11 wherein said shank has a longitudinal axis and said pin is disposed coaxially on said axis.

13. The combination as set forth in claim 10 which further comprises means for interfitting said element with said shank to prevent relative rotation therebetween.

14. The combination as set forth in claim 13 wherein said interfitting means includes a contact area on said shank and a noselike extension on a part of said base abutting said contact area.

15. The combination as set forth in claim 10 which further comprises a neck extending from said shank along a second axis disposed in a common plane with said axis of said shank.

16. The combination as set forth in claim 15 wherein said shank has a contact area at a distal end perpendicular to said common plane and said centering element has a noselike extension abutting said contact area to align a corner of said element in said common plane and laterally of said neck.

17. The combination as set forth in claim 10 wherein each side of said centering element has a concave curvature.

18. The combination as set forth in claim 17 wherein said centering element has a rounded apex.

* * * * *